United States Patent [19]

Satek et al.

[11] Patent Number: 5,084,259
[45] Date of Patent: Jan. 28, 1992

[54] CRYSTALLINE NICKEL ALUMINUM BORATES

[75] Inventors: Larry C. Satek, Wheaton; Stephen T. McKenna, Lisle; Vincent F. Smith, Jr., Big Rock, all of Ill.

[73] Assignee: Amoco Corporation, Chicago, Ill.

[21] Appl. No.: 669,903

[22] Filed: Mar. 15, 1991

Related U.S. Application Data

[63] Continuation of Ser. No. 233,266, Aug. 17, 1988, abandoned.

[51] Int. Cl.$^5$ ............................................. C01B 35/12
[52] U.S. Cl. .................................. 423/277; 423/328;
502/60; 502/64; 502/66; 502/412; 568/435;
585/440; 585/525; 585/531; 585/533
[58] Field of Search ............... 423/277, 278, 279, 328,
423/213.5, 115, 121; 502/66, 64, 60; 208/46;
562/412; 568/435; 585/440, 525, 531, 533

[56] References Cited

U.S. PATENT DOCUMENTS

| | | | |
|---|---|---|---|
| 3,856,702 | 12/1974 | McArthur | 423/279 |
| 3,856,705 | 12/1974 | McArthur | 423/279 |
| 3,954,670 | 5/1976 | Pine | 502/66 |
| 4,024,171 | 5/1977 | McArthur | 423/213.5 |
| 4,034,061 | 7/1977 | McArthur | 423/213.5 |
| 4,645,753 | 2/1987 | Zletz et al. | 423/279 |
| 4,767,738 | 8/1988 | Melquist et al. | 423/279 |

OTHER PUBLICATIONS

Schwab et al., "Structure du boroaluminate B$_2$O$_3$.Al$_2$O$_3$.4NiO" Bull. Soc. Fr. Mineral. Crystallogr. (1970) pp. 255-257.

Primary Examiner—R. Bruce Breneman
Attorney, Agent, or Firm—Frederick S. Jerome; William H. Magidson; Ralph C. Medhurst

[57] ABSTRACT

The preparation, structure, and properties of solid inorganic materials containing aluminum, boron, oxygen and at least one Group VIII metallo element, selected from the group consisting of cobalt and nickel is described. Also described in the use of such materials in catalytic compositions for the conversion of organic compounds. In particular, the new materials having the general formula:

$$(x)\,(M_m{:}M'_n)O.(y)Al_2O_3.(z)B_2O_3$$

where M and M' are metallo elements selected from the group consisting of nickel and cobalt, m and n are numbers from 0 to 1 inclusive, such that $m+n=1$, and x, y and z are numbers representing molar amounts of the oxides are described as well as the use of such materials in various catalyzed processes including hydrogenation of hydrocarbons and oxygen containing hydrocarbons, dehydrogenation to functionalize alkylaromatic compounds, isomerization of alkylaromatic compounds, oligomerization of olefins, and oxidation of hydrocarbons and oxygen containing hydrocarbons.

9 Claims, No Drawings

CRYSTALLINE NICKEL ALUMINUM BORATES

This is a continuation of application Ser. No. 07/233,266, filed Aug. 17, 1988, now abandoned.

BACKGROUND OF THE INVENTION

The present invention relates to crystalline inorganic materials containing at least one Group VIII metallo element selected from the group consisting of cobalt and nickel, aluminum, boron and oxygen having specified X-ray patterns. This invention also relates to solid inorganic materials containing at least one Group VIII metallo element, aluminum, boron and oxygen made by calcining a mixture comprising sources of divalent metallo ions, alumina and boria at elevated temperature, and the use of such solid in catalytic compositions for the conversion of organic compounds, particularly hydrogenation of hydrocarbons and oxygen containing hydrocarbons, dehydrogenation to functionalize alkylaromatic compounds, isomerization of alkylaromatic compounds, oligomerization of olefins, and oxidation of hydrocarbons and oxygen containing hydrocarbons.

The use of an active metallo element or a supported metallo element composition containing aluminum and boron as a conversion catalyst is known in the art. U.S. Pat. No. 3,883,442 to McArthur is illustrative of prior art disclosing the superiority of a supported active metal catalyst to resist shrinkage at high temperatures (up to 1600° C.) by stabilization of a preformed alumina catalyst support. McArthur states stabilization was achieved by impregnating an alumina support with a solution of a boron compound which is thermally decomposable to $B_2O_3$, followed by drying and calcining of the impregnated support at temperatures below about 1500° C., but sufficiently high to decompose the boron compound. McArthur also discloses that the most commonly used technique of preparing a supported metallo element catalyst involved: following calcination, impregnating in conventional manner the alumina support material containing some retained $B_2O_3$ with a solution of the desired metal salt, preferably those that are thermally decomposable to give the corresponding metal oxides and/or sulfides, and calcining the salt-impregnated support to convert the impregnated salt to the active catalytic form. McArthur neither discloses nor suggests a mixed oxide composition of a metallo element, aluminum, and boron.

In U.S. Pat. No. 3,954,670 to Pine a boria-alumina based catalyst is disclosed in the combination of a metallo element and a boria-alumina catalyst support materials prepared by hydrolysis of a mixture of aluminum alkoxide and boron alkoxide in the presence of water at a temperature in the range of 20° to 100° C. The disclosed catalyst compositions, said to be useful for desulfurization, denitrogenation, reforming and other hydrocarbon conversion processes, included both cobalt and nickel as metallo elements in combinations with the boria-alumina catalyst composition disclosed in Pine and, optionally, a crystalline aluminosilicate zeolite with or without rare earth elements. However, Pine neither discloses nor suggests any crystalline mixed oxide composition of a metallo element, aluminum, and boron.

Zletz in U.S. Pat. No. 4,729,979, which is hereby incorporated by reference, discusses the characteristics of a good catalyst and/or catalyst support and a new crystalline copper aluminum borate characterized by a specific X-ray diffraction pattern, surface area and pore volume which is at least partially reducible with hydrogen at a temperature no more than 350° C., to a composition containing zero valent copper and $Al_4B_2O_9$. Satek in U.S. Pat. No. 4,590,324, which is hereby incorporated by reference, discusses using the new crystalline copper aluminum borate as a catalyst to dehydrogenate alkylaromatics to alkenylaromatics. Zletz et al. in U.S. Pat. No. 4,645,753, which is hereby incorporated by reference, discusses doping the new crystalline copper aluminum borate to contain an alkali metal or alkaline earth metal element for use as a catalyst to dehydrogenate alkylaromatics to alkenylaromatics. The Zletz, Satek, and Zletz et al. patents alone or in combination neither disclose nor suggest a mixed oxide composition of aluminum, boron, and a metallo element without copper. Furthermore, these patents disclose crystalline copper aluminum borate having significant X-ray diffraction lines which are substantially different from X-ray diffraction patterns for crystalline materials of the present invention.

Schwab and Bertaut disclose the preparation of a single crystal of a boroaluminate of nickel in *Bull. Soc. Fr. Mineral. Cristollogr.* (1970), 93, 255–257, "Structure di boroaluminate $B_2O_3.Al_2O_3.4NiO$" which is hereby incorporated by reference, by mixing the oxides $B_2O_3$, $Al_2O_3$ and NiO in the mol ratio of 1:1:4 plus a large excess of $B_2O_3$ [sic], heating the mixture to 1300° C., cooling the hot mixture carefully to room temperature at a rate of 50° C. per hour, and treating the cooled product with dilute nitric acid to dissolve excess borax providing single crystals about 2–3 mm long. The atomic coordinates for a single crystal structure are reported, however no powder x-ray diffraction pattern is reported. Boroaluminates of nickel produced by the indicated route are believed to be well-defined, dense crystalline particles which have an extremely low surface area due to heating a mixture of oxides to a temperature of 1300° C.

The general object of the present invention is to provide a new composition useful as a catalyst to convert organic compounds to other compounds.

Another general object of this invention is to produce a new catalyst which is useful to hydrogenate hydrocarbons and oxygen containing hydrocarbons, dehydrogenate alkylaromatic compounds, isomerize alkylaromatic compounds, oligomerize olefins, and oxidize hydrocarbons, particularly aromatic hydrocarbons.

Other objects and advantages of the invention will become apparent upon reading the following detailed description and appended claims.

SUMMARY OF THE INVENTION

In one aspect, the present invention is a crystalline inorganic material comprising aluminum, boron, oxygen and at least one Group VIII metallo element, preferably selected from the group consisting of cobalt and nickel having an X-ray diffraction pattern comprising significant lines substantially as shown in at least one of the tables set out herein as Table I, Table II, Table III and Table IV.

In another aspect, the invention describes the preparation and properties of a crystalline inorganic material comprising aluminum, boron, oxygen and at least one Group VIII metallo element, preferably selected from the group consisting of cobalt and nickel made by calcining a mixture containing sources of divalent nickel ions and/or divalent cobalt ions, alumina and boria at elevated temperature, the solid providing an X-ray pattern comprising lines substantially as shown in at least one of the tables set out herein as Table I, Table II, Table III and Table IV.

In a preferred embodiment the present invention is a crystalline inorganic material comprising aluminum, boron, oxygen and nickel having an X-ray diffraction pattern comprising significant lines substantially as shown in Table I.

TABLE I

Principal XRD Lines

| Interplanar Spacing[1] d, Å | Assigned Strength[2] |
|---|---|
| 6.41 ± 0.2 | W |
| 4.09 ± 0.10 | M |
| 2.90 ± 0.08 | M |
| 2.53 ± 0.05 | M |
| 2.50 ± 0.05 | VS |
| 1.92 ± 0.05 | W |
| 1.74 ± 0.04 | W |
| 1.55 ± 0.04 | W |
| 1.50 ± 0.04 | W |
| 1.46 ± 0.03 | W |

[1]Angstroms
[2]VW = very weak; W = weak; M = medium; S = strong; VS = very strong As is generally known, the assigned strengths in X-ray diffraction patterns may vary depending upon the characteristics of the sample. The observed line strength in any particular sample may vary from another sample. Also, X-ray diffraction lines of a particular crystalline material may be obscured by lines from other materials present in a measured sample.

In another aspect, the invention describes the preparation and properties of a solid inorganic material containing nickel, aluminum, boron and oxygen having the empirical formula $NiAlBO_4$ and providing an X-ray pattern comprising the X-ray diffraction lines and assigned strengths shown in Table I.

Another preferred embodiment of the present invention is a crystalline inorganic material prepared as described above to form a solid composition containing nickel, aluminum, boron and oxygen having an X-ray diffraction pattern comprising lines substantially as shown in Table II.

TABLE II

Principal XRD Lines

| Interplanar Spacing[1] d, Å | Assigned Strength[2] |
|---|---|
| 5.01 ± 0.2 | M |
| 4.55 ± 0.15 | M |
| 3.66 ± 0.08 | W |
| 2.51 ± 0.05 | S |
| 2.47 ± 0.05 | VS |
| 2.29 ± 0.05 | M |
| 2.12 ± 0.05 | W |
| 2.08 ± 0.05 | W |
| 1.99 ± 0.05 | M |
| 1.87 ± 0.05 | M |
| 1.54 ± 0.04 | W |
| 1.47 ± 0.04 | W |
| 1.46 ± 0.03 | M |
| 1.44 ± 0.03 | W |

[1]Angstroms
[2]VW = very weak; W = weak; M = medium; S = strong; VS = very strong In another aspect, the invention describes the preparation and properties of a solid inorganic material containing nickel, aluminum, boron and oxygen having the empirical formula $Ni_2AlBO_5$ and providing an X-ray pattern comprising the X-ray diffraction lines and assigned strengths shown in Table II.

In another preferred embodiment of the present invention is a crystalline inorganic material containing cobalt, aluminum, boron and oxygen having an X-ray diffraction pattern comprising lines substantially as shown in Table III.

TABLE III

Principal XRD Lines

| Interplanar Spacing[1] d, Å | Assigned Strength[2] |
|---|---|
| 5.03 ± 0.2 | M |
| 4.60 ± 0.15 | M |
| 3.68 ± 0.10 | W |
| 2.52 ± 0.06 | VS |
| 2.32 ± 0.05 | W |
| 2.30 ± 0.05 | W |
| 2.12 ± 0.05 | W |
| 2.02 ± 0.04 | W |
| 1.89 ± 0.05 | M |
| 1.56 ± 0.04 | W |
| 1.50 ± 0.04 | W |
| 1.47 ± 0.03 | W |
| 1.37 ± 0.02 | W |

[1]Angstroms
[2]VW = very weak; W = weak; M = medium; S = strong; VS = very strong In another aspect, the invention describes the preparation and properties of a solid inorganic material containing cobalt, aluminum, boron and oxygen having the empirical formula $Co_2AlBO_5$ and providing an X-ray pattern comprising the X-ray diffraction lines and assigned strengths shown in Table III.

Another preferred embodiment of the present invention is a crystalline inorganic material prepared as described above to form a solid composition containing cobalt, nickel, aluminum, boron and oxygen having an X-ray diffraction pattern comprising lines substantially as shown in Table IV.

TABLE IV

Principal XRD Lines

| Interplanar Spacing[1] d, Å | Assigned Strength[2] |
|---|---|
| 5.02 ± 0.2 | M |
| 4.57 ± 0.15 | M |
| 3.66 ± 0.10 | W |
| 2.51 ± 0.05 | S-VS |
| 2.48 ± 0.05 | S-VS |
| 2.30 ± 0.05 | M |
| 2.00 ± 0.05 | M-W |
| 1.88 ± 0.05 | M-W |

[1]Angstroms
[2]VW = very weak; W = weak; M-W = medium to weak; M = medium; S = strong; S-VS = strong to very strong; VS = very strong Another aspect of the invention describes the preparation and properties of a solid material having the empirical formula $$4(Co_m:Ni_n)O \cdot Al_2O_3 \cdot B_2O_3$$

where m and n are numbers from 0.0 to 1.0 such that m+n=1 and providing an X-ray pattern comprising the X-ray diffraction lines and assigned strengths shown in Table IV.

In still another aspect, the invention describes the use of such solid materials in catalytic compositions for the conversion of organic compounds. In a further aspect, the invention describes the use of such materials for hydrogenation of hydrocarbons and oxygen containing hydrocarbons, for example in the conversion of aromatic esters to the corresponding aldehydes. In a further aspect, the invention describes the use of such materials for dehydrogenation of alkylaromatic compounds. In a further aspect, the invention describes the use of such materials for isomerization of alkylaromatic compounds. In a further aspect, the invention describes the use of such materials for oligomerization of olefins, and in still a further aspect, the invention describes the use of such materials for oxidizing and/or partially oxidizing one or more oxidizable substituents on an aromatic compound with the aromatic compound in a fluid-phase to form a partially oxidized aromatic product and/or a carboxylic acid derivative.

DETAILED DESCRIPTION OF THE INVENTION

The nickel and/or cobalt, aluminum, boron, and oxygen solid materials of the present invention can be prepared by calcining a mixture of source of nickel(II) and/or cobalt (II) ions, a source of alumina, and a source of boria.

Conditions of calcination include a temperature within the range of about 600° C. to about 1500° C., a pressure of at least about one atmosphere, and a reaction time that is sufficient to affect formation of a crystalline metalloaluminum borate. Increasing pressure and temperature of calcination, generally affect formation of a crystalline metalloaluminum borate in a shorter reaction time. However, a high temperature of calcination typically results in crystalline materials with less desirably surface properties, for example low surface area. Preferred calcination temperatures are in a range of about 700° C. to 1100° C. Calcination can be carried out in air, nitrogen or other inert gases. A preferred atmosphere for calcination contains oxygen.

The solid materials of this invention can be prepared generally by dispersing the required ingredients in a liquid medium, preferably an aqueous medium, removing substantially all the liquid to form superficially dry mixture, and calcining the dry mixture.

When a liquid medium is used, the source of nickel(II) or cobalt(II) ions can be any reasonably soluble salt of nickel(II), cobalt(II), or precursor thereof which is at least partially soluble in the dispersing liquid, such as the acetate, formate, carbonate, chloride, bromide, sulfate and the like. Nickel(II) and cobalt(II) salts containing a decomposable anion such as nickel nitrate, nickel acetate, nickel formate, nickel carbonate, cobalt nitrate, cobalt acetate, cobalt formate, cobalt carbonate, etc. are preferred.

Typically, best results are obtained when each of the sources used is chosen to reduce the content of foreign anions and cations in the reaction mix.

The source of alumina is any material capable of producing alumina, but preferred is a well dispersed, liquid source such as an alumina sol.

The source of boria is a material such as borate or boric acid with pure boric acid being preferred.

Typically, the mole ratios of the various reactants can be varied to produce the solid of this invention. Specifically, the mole ratios in terms of oxides of the initial reactant concentrations are characterized by the general mixed oxide formula

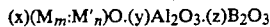

$(x)(M_m:M'_n)O\cdot(y)Al_2O_3\cdot(z)B_2O_3$ where M and M' are metallo elements selected from the group consisting of nickel and cobalt, m and n are numbers from 0.0 to 1.0, inclusive, such that $m+n=1$, and x, y and z are numbers representing molar amounts of the oxides of the source reagents. A preferred ratio of m/n is in a range of about 0.01 to about 0.5. A preferred ratio of n/m is in a range of about 0.01 to about 0.5. The mole ratios of $(M_m:M'_n)O/B_2O_3$, calculated as x/z are about 0.1 to about 100, preferably about 0.15 to about 40, and most preferably about 0.2 to about 20, and the mole ratios of $Al_2O_3/B_2O_3$, calculated as y/z can range up to about 20, preferably about 0.01 to about 10 and more preferably about 0.02 to about 5.

In somewhat greater detail, a preferred procedure is to dissolve the boria source and disperse the alumina source in water with mixing in a blender for about 3-5 minutes, then adding an aqueous solution of a source of a Group VIII metallo element to the blender followed by gelation with ammonia.

Typically, the pH of the aqueous mixture is less than about 11. If the reaction media is too acid or too basic, the desired solid generally will not form or other contaminating phases are formed in addition to the desired product. To some extent the pH of the reaction mixture controls surface properties of the final calcined solid material. Preferably, the pH of the reaction mixture is in a range from about 3 to about 10, more preferably about 4 to about 9, in order to gel the reaction mixture. If desired, the pH can be adjusted with a base such as ammonia, ethylenediamine, tetramethylammonium hydroxide and the like. Preferred is the use of ammonium hydroxide. The presence of the ammonia as well as other volatile components in the gelled mixture, such as acetate ion, nitrate ion, etc., is advantageous in providing the final calcined solid with sufficiently high surface area and porosity desirable for catalytic reactions.

The gelled mixture is allowed to air dry, usually for about 1-3 days, followed by vacuum drying, typically at a pressure of about 0.3 atmosphere for about 15 to 25 hours at about 100° C. to 150° C. with a nitrogen purge.

The superficially dry mixture is calcined, preferably at a temperature within the range of about 700° to about 1100° C. for a reaction time that is sufficient to affect formation of a crystalline metalloaluminum borate, typically a reaction time within the range of about 2 to about 30 hr. Samples of material can be removed during calcination to check the degree of crystallization and determine the optimum calcination time.

The crystalline material formed can be crushed to a powder or to small particles and extruded, pelletized, or made into other forms suitable for its intended use. In a preferred embodiment of the above-described method, the crystalline material formed can be washed with a solvent, preferably an aqueous solvent, which removes impurities such as excess boria, without destroying the crystalline material formed, mildly dried for anywhere from a few hours to a few days at varying temperatures, typically about 50° to about 225° C., to form a dry cake which can then be treated as required for its intended use.

The solid materials made by this invention can be admixed with or incorporated within various binders or matrix materials depending upon the intended process use. They are combined with active or inactive materials, synthetic or naturally occurring oxides, as well as inorganic or organic materials which would be useful for binding such substances. Well-known materials include silica, silica-alumina, alumina, magnesia, titania, zirconia, alumina sols, hydrated aluminas, clays such as bentonite or kaolin, Sterotex (a powdered vegtable stearine produced by Capital City Products, Co., Columbus, Ohio), or other binders well known in the art.

Advantageously, a crystalline material formed according to this invention is formed or combined with from about 0.05 to about 50 wt % of at least one compound of a metallo element selected from the group consisting of Groups IA, IIA, IIB, and IIIB of the Periodic Table based on the weight of crystalline material. The Periodic Table is the well known arrangement of chemical elements based on the periodic law and is found in *Webster's Ninth New Collegiate Dictionary*, Merriam-Webster Inc., Springfield, Mass., U.S.A., (1984) at page 874.

Suitable alkali metal (Group IA), alkaline earth metal (Group IIA), low melting metal (Group IIB) and heavy metal (Group IIIB) compounds including rare earth compounds of elements in the lanthanide series and actinide series include the oxides, hydroxides and salts of lithium, sodium, potassium, rubidium, cesium, magnesium, calcium, strontium, barium, zinc, cadmium, lanthanum, cerium, and thorium, such as lithium hydroxide, sodium hydroxide, potassium hydroxide, magnesium hydroxide, potassium oxide, sodium oxide, potassium carbonate, sodium carbonate, sodium bicarbonate, potassium nitrate, potassium borate, sodium borate, potassium chloride, potassium acetate, sodium propionate, potassium maleate, etc. of these, potassium, in the form of the oxide or in a form readily convertible to the oxide, is preferred. The solid materials formed according to this invention can be treated with from about 0.05 to 50 wt % dopant based on the weight of the solid material. The alkali metal or alkaline earth metal compound can be dry-blended with the aluminum borate, dissolved in a suitable solvent, preferably water, mixed with the solid material and dried; or aqueous solutions of same can be added to feedstocks going to a reactor containing the solid material catalyst.

Catalyst compositions of this invention are useful generally in the chemical conversion of organic compounds, particularly hydrocarbon and oxygenated hydrocarbon. In particular, chemical conversion reactions such as hydrogenation, dehydrogenation, isomerization, oligomerization and oxidation have been carried out. Crystalline materials of this invention have been used for hydrogenation of methylbenzoate to benzaldehyde, for dehydrogenation of methylcyclohexane to toluene, for dehydrogenation to functionalize alkylaromatic compounds ethylbenzene to styrene, cumene to alpha-methylstyrene, and p-ethyltoluene to p-methylstryene, for oligomerization of ethylene to linear butenes and propylene to hexenes, for isomerization of o-xylene and for oxidation and/or partial oxidation of p-xylene to oxygenated aromatic products.

Particularly useful is the fact that when these solid catalyst compositions are used in liquid and/or gas phase processes, the products of chemical conversion are easily separated from the solid catalyst material. Also useful is the fact that when these solid catalyst compositions are used in such fluid-phase processes, the active metallo element components are only slowly extracted, leading to longer catalyst lifetime.

Generally a process of the present invention for chemical conversion comprising contacting under suitable reaction conditions an organic reactant in a fluid phase, i.e. liquid and/or vapor phase, with a heterogeneous catalyst composition comprising a crystalline material having a chemical composition:

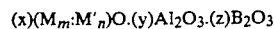

where M and M' are metallo elements selected from the group consisting of nickel and cobalt, m and n are numbers from 0 to 1, inclusive, such that $m+n=1$, and x, y and z are numbers representing molar amounts of the oxides and containing a crystalline metalloaluminum borate having an X-ray diffraction pattern comprising significant lines substantially as described in at least one of the tables I–IV, inclusive.

The following examples will serve to illustrate certain specific embodiments of the herein disclosed invention. These examples should not, however, be construed as limiting the scope of the novel invention, as there are many variations which may be made thereon without departing from the spirit of the disclosed invention, as those of skill in the art will recognize.

For example, a process for oxidation in the presence of the above-described catalyst compositions is effected by contact of the organic compound either in the liquid or vapor phase at temperatures ranging from about 50° C. to about 1000° C. Generally, an oxygen-containing gas is used as the oxidant. Air can be used or synthetic mixture of an inert gas and oxygen made so as to adjust the oxygen level to the desired amount. The reaction takes place at atmospheric pressure, but the pressure may be within the range of about 0 to 2000 psig. Reaction is suitably accomplished using a weight hourly space velocity between about 0.01 and about 100 hr$^{-1}$. For some compounds, reaction in the liquid phase is preferred. Reactions in the liquid phase typically are carried out at about 50° C. to about 400° C., preferably at about 75° C. to about 360° C. and most preferably at about 100° C. to about 250° C., with pressures of about 0 to about 500 psig, preferably about 40 to about 350 psig at space velocities from about 0.02 to about 5 hr$^{-1}$, preferably about 0.08 to about 2 hr$^{-1}$. Liquid phase reactions can be carried out in a trickle bed configuration, catalytic distillation configuration or slurry bed configuration, for example. Gas phase reactions typically are carried out at about 200° C. to about 1000° C., preferably about 300° C. to about 600° C. and most preferably at about 400° C. to about 500° C., with pressures of about 0 to about 300 psig and space velocities of about 0.01 to about 100 hr$^{-1}$, preferably about 0.5 to about 50 hr$^{-1}$. Gas phase reactions can be carried out in a fluid bed, stirred bed, fixed bed or other suitable reactor configuration.

In the context of the present invention, "partial oxidation" means either oxidation of less than all of the oxidizable groups on an organic reactant or the oxidation of up to all of the oxidizable groups but not completely to the carboxylic acid derivative.

A suitable feed for use in the oxidation and/or partial oxidation processes of this invention comprises an aromatic reactant having at least one phenyl ring or a condensed aromatic ring system and substituted with at least one oxidizable substituent selected from the group consisting of alkyl, hydroxyalkyl, aldehyde, ketone groups and mixtures thereof. Each such alkyl group or the alkyl moiety of each hydroxyalkyl group contains from 1 to 3 carbon atoms and preferably contains one carbon atom. Preferably each oxidizable substituent is a methyl group. Thus, such typical aromatic reactants include toluene, o-, m-, or p-xylene, pseudocumene, durene, ethylbenzene, o-, m-, p-diethylbenzene, 1,2,4-triethylbenzene, 1,2,4,5-tetraethylbenzene, a propylbenzene, o-, m-, or p-dipropylbenzene, 1,2,4-triproplybenzene, 1,2,4,5-tetrapropylbenzene, a methyl-, ethyl- or propylnaphthalene, a di-(methyl-, or ethyl-, or propyl-) naphthalene, 4,4'-dimethylbiphenyl, 4,4'-dimethyldiphenyl ether or sulfone, 3,3',4,4'-tetramenthybiphenyl, 3,3',4,4'-dimethyldiphenyl ether or sulfone, or 3,3',4,4'-tetramethyldiphenylpropane. Preferably the aromatic reactant is p-xylene, m-xylene, pseudocumene, durene, a dimethylnaphthalene, a di-isopropylnaphthalene, or 4,4'-dimethyldiphenyl ether or sulfone, 3,3',4,4'tetramethyldiphenyl ether or sulfone, or 3,3',4,4'-tetramethyldiphenyl propane.

Although the feed can comprise a solvent, such as chlorobenzene, for the aromatic reactant, preferably a solvent is not employed. The aromatic feed comprises preferably at least 80 weight percent, more preferably at least 90 weight percent of the feed, in order to avoid any extensive purification of the oxidation products. Preferably the feed consists essentially of the aromatic reactant.

Nickel aluminum borate prepared according to the procedures outlined above is an active catalyst for dehydrogenation/hydrogenation reactions in which a suitable hydrocarbon is converted to styrene, alpha-methylstyrene, or benzaldehyde.

Cobalt aluminum borate prepared according to the procedures outlined above is an active catalyst for reactions in which a suitable hydrocarbon is converted to benzaldehyde.

Cobalt and/or nickel aluminum borates prepared according to the procedures outlined above are active catalysts for oxidation reactions in which a suitable hydrocarbon is converted to a partially oxidized product and/or to the carboxylic acid derivative.

Cobalt/nickel aluminum borate prepared according to the procedures outlined above is an active catalyst for dehydrogenation/hydrogenation reactions in which a suitable hydrocarbon is converted to styrene, alpha-methylstyrene, or benzaldehyde.

A process for the hydrogenation of methylbenzoate comprises contacting hydrogen and methylbenzoate in the vapor state with a solid material containing cobalt and/or nickel, aluminum, boron and oxygen according to this invention. Suitable conditions for the hydrogenation of methylbenzoate comprise a pressure of about 0.5 atmospheres to about 100 atmospheres, preferably about 1 atmospheres to about 20 atmospheres, a temperature upward from the vaporization temperature of the feedstream at operating conditions to about 600° C., preferably about 200° C. to about 500° C., most preferably about 300° C. to 400° C., and a weight hourly space velocity (WHSV) of about 0.01 to about 100 $hr^{-1}$, preferably about 0.1 to about 10 $hr^{-1}$.

A process for the dehydrogenation of ethylbenzene comprises contacting a feedstream containing ethylbenzene in the vapor state with a solid material containing cobalt and/or nickel, aluminum, boron and oxygen according to this invention. Suitable conditions for the dehydrogenation of ethylbenzene comprise a pressure of about 0.5 atmospheres to about 100 atmospheres, preferably about 1 atmospheres to about 20 atmospheres, a temperature upward from the vaporization temperature of the feedstream at operating conditions to about 900° C., preferably about 500° C. to about 700° C., most preferably about 550° C. to 650° C., and a liquid hourly space velocity (LHSV) of about 0.01 to about 100 $hr^{-1}$, preferably about 0.1 to about 10 $hr^{-1}$. Advantageously, the feedstream also contains a diluent such as steam or an inert gas. The weight ratio of diluent to hydrocarbon may be any suitable value, preferably in a range from about 0.1 to about 10, most preferably about 0.5 to about 5.

A process for the oligomerization of olefinic hydrocarbons comprises contacting a feedstream containing a light olefin such as ethylene and/or propylene in the vapor state with a solid material containing cobalt and/or nickel, aluminum, boron and oxygen according to this invention. Suitable conditions for the oligomerization of olefinic hydrocarbons comprise a pressure of about 0.5 atmosphere to about 100 atmosphere, preferably about 1 atmospheres to about 20 atmospheres, a temperature upward from the vaporization temperature of the feedstream at operating conditions to about 800° C., preferably about 100° C. to about 600° C., most preferably about 200° C. to 400° C., and a weight hourly space velocity (WHSV) of about 0.1 to about 20 $hr^{-1}$, preferably about 0.5 to about 5 $hr^{-1}$. The feedstream may also contain inert diluents such as paraffinic hydrocarbons and/or nitrogen or other inert gas.

EXAMPLE 1

A crystalline inorganic material was prepared containing nickel, aluminum, boron and oxygen in accordance with this invention by a process including five steps: 1) combining ingredients in a liquid medium, 2) gelling the combined ingredients, 3) removing substantially all the liquid to obtain a dry solid, 4) calcining the dry solid, and 5) washing the calcined solid.

The ingredients placed into a Waring blender were 72.7 g Ni($NO_3$)$_2$—6$H_2O$ (0.250 mol) dissolved in 75 mL warm distilled water, 193.7 g of alumina sol (7.9% alumina, 0.150 mol) and 74.2 g $H_3BO_3$ (1.20 mol) dissolved in 375 mL warm distilled water. These ingredients were blended for 2 minutes. The resulting mixture had a pH of about 3.5–4.0. Ammonium hydroxide, 54 mL, was added and the material was blended for four minutes. The mint green gel had a final pH of 7.0–7.2. The gel was placed evenly on a 35 cm×45 cm plastic tray and allowed to air dry. A portion, 155.47 g, of the material was placed in a vacuum oven at 120 degrees C., 0.3 atm pressure with a nitrogen purge and dried to a final weight of 111.0 g. A portion of this solid, 102.3 g, was calcined according to the following program:

$$120\ C. \xrightarrow{1\ hr} 300\ C. \xrightarrow{3\ hrs} 780\ C. \xrightarrow{8\ hrs}$$

$$780\ C. \xrightarrow{3\ hrs} 300\ C. \xrightarrow{1\ hr} 120\ C. \xrightarrow{1\ hr} 25\ C.$$

This resulted in 60.81 g of calcined material. Part of the mass (59.1 g) was placed in a 2 L round bottom flask containing 1450 mL distilled water, and the mixture was refluxed for 6 hours. The gray solid was removed by filtration and dried at 120 degrees C., 0.3 atm pressure with a nitrogen purge for 6 hours. The resulting solid weighted 33.6 g. This product was analyzed by powder XRD, ICP elemental analysis and BET surface analysis. Elemental analysis showed 33.2% nickel, 17.8% aluminum, and 6.4% boron which indicates that the crystalline material has the chemical composition $NiAlBO_4$. The BET surface area was determined to be 38 $m^2/g$ and the pore volume was 0.16 cc/g. The powder XRD pattern is set out below:

| XRD Lines for NiAlBO4 | | |
|---|---|---|
| Interplanar Spacing[1] d, Å | Assigned Strength[2] | Relative Intensity |
| 6.41 ± 0.2 | W | 20 |
| 4.46 ± 0.1 | VW | 4 |
| 4.09 ± 0.08 | M | 41 |
| 4.02 ± 0.08 | VW | 11 |
| 2.90 ± 0.05 | M | 29 |
| 2.53 ± 0.05 | M | 46 |
| 2.50 ± 0.05 | VS | 100 |
| 2.42 ± 0.04 | VW | 8 |
| 2.40 ± 0.04 | VW | 9 |
| 2.09 ± 0.03 | VW | 7 |
| 2.06 ± 0.03 | VW | 8 |
| 2.04 ± 0.03 | VW | 9 |
| 1.92 ± 0.03 | W | 19 |
| 1.80 ± 0.03 | VW | 11 |
| 1.74 ± 0.02 | W | 20 |
| 1.55 ± 0.02 | W | 22 |
| 1.50 ± 0.02 | W | 16 |
| 1.46 ± 0.02 | W | 19 |
| 1.35 ± 0.02 | VW | 11 |

[1] Angstroms
[2] VW = very weak; W = weak; M = medium; S = strong; VS = very strong

EXAMPLE 2

Example 1 was repeated except the amount of each ingredient was increased by a factor of four using a larger blender. The BET surface area of this material was determined to be 46 m$^2$/g.

EXAMPLE 3

Example 1 was repeated except the time of washing the calcined solid reduced to 3 hours. This product was analyzed by powder XRD and ICP elemental analysis. The XRD pattern was essentially the same as the pattern of Example 1. Elemental analysis showed 35.0% nickel, 17.1% aluminum, and 7.2% boron.

EXAMPLE 4

Example 1 was repeated except washing of the calcined solid for 2 hours in 6M nitric acid at 60° C. This product was analyzed by powder XRD. The XRD pattern was essentially the same as the pattern of Example 1.

EXAMPLE 5

The ingredients placed into a Waring blender were 290.8 g Ni(NO3)2—6H2O (1 mol) dissolved in 300 mL warm distilled water, 774.7 g of alumina sol (7.9% alumina, 0.6 mol) and 296.8 g H3BO3 (4.8 mol) dissolved in 1500 mL warm distilled water. These ingredients were blended for 2 minutes. The resulting mixture had a pH of about 3.5-4.0. A total of 400 mL of ammonium hydroxide was added and the material was blended. The mint green gel had a final pH of 9.0. The gel was placed evenly on a tray and allowed to air dry. A portion, 542.1 g, of the material was placed in a vacuum oven at 120° C., 0.3 atm pressure with a nitrogen purge and dried to a final weight of 451.9 g. A portion of this solid, 113.7 g, was calcined according to the following program:

$$120\ C. \xrightarrow{1\ hr} 300\ C. \xrightarrow{3\ hrs} 780\ C. \xrightarrow{8\ hrs}$$

$$780\ C. \xrightarrow{3\ hrs} 300\ C. \xrightarrow{1\ hr} 120\ C. \xrightarrow{1\ hr} 25\ C.$$

This resulted in 66.9 g of calcined material. Part of the mass (66.8 g) was placed in a 2 L round bottom flask containing 1500 mL distilled water, and the mixture was refluxed for 6 hours. The gray solid was removed by filtration and dried at 120° C., 0.3 atm pressure with a nitrogen purge for 18 hours. The resulting solid weights 38.6 g. This product was analyzed by powder XRD, ICP elemental analysis and BET surface analysis. The XRD pattern was similar to the pattern of Example 1. Elemental analysis showed 33.3% nickel, 18.3% aluminum, and 6.9% boron. The BET surface area was determined to be 46 m$^2$/g and the pore volume was 0.19 cc/g. This material was treated with Th(NO3)4 using the incipient wetness technique. A portion of the solid material, 5 g, and 0.595 g of Th(NO3)4 dissolved in minimal distilled water were placed in a crucible. The crucible was placed in a microwave oven and the wet solid was irradiated until dryness. The dry solid was then calcined to 400° C. for 6 hours to remove the nitrates. The doped material contained 5% ThO2 and was labeled Example 5.

EXAMPLE 6

A crystalline inorganic material was prepared containing nickel, aluminum, boron and oxygen in accordance with this invention by a process including five steps: 1) combining ingredients in a liquid medium, 2) gelling the combined ingredients, 3) removing substantially all the liquid to obtain a dry solid, 4) calcining the dry solid, and 5) washing the calcined solid.

The ingredients placed into a Waring blender were 116.3 g Ni(NO3)2—6H2O (0.400 mol) dissolved in 120 mL warm distilled water, 129.1 g of alumina sol (7.9% alumina, 0.100 mol) and 61.8 g H3BO3 (1.00 mol) dissolved in 300 mL warm distilled water. The contents of the blender were mixed for 2 minutes. The resulting mixture had a pH of about 3.5-4.0. Ammonium hydroxide, 45 mL, was added and the material was mixed for four minutes. The mint green gel had a final pH of 6.4. The gel was placed evenly on a 35 cm×45 cm plastic tray and allowed to air dry. A portion, 180.37 g, of the material was placed in a vacuum oven at 120° C., 0.3 atm pressure with a nitrogen purge and was dried to a final weight of 121.6 g. A portion of this solid, 113.7 g, was calcined according to the following program:

$$120\ C. \xrightarrow{1\ hr} 165\ C. \xrightarrow{3\ hrs} 780\ C. \xrightarrow{8\ hrs}$$

$$780\ C. \xrightarrow{3\ hrs} 165\ C. \xrightarrow{1\ hr} 120\ C. \xrightarrow{1\ hr} 25\ C.$$

This resulted in 59.29 g of calcined material. The entire mass was placed in a 2 L round bottom flask containing 1450 mL distilled water, and the mixture was refluxed for 6 hours. The gray solid was removed by filtration and dried at 120° C., 0.3 atm pressure with a nitrogen purge for 6 hours. The resulting solid weighed 30.5 g. This product was analyzed by powder XRD, ICP elemental analysis and BET surface analysis. Elemental analysis showed 47.3% nickel, 11.2% aluminum, and 5.2% boron which indicates that the crystalline material has the chemical composition Ni2AlBO5. The BET surface area chemical composition Ni2AlBO5. The BET surface area was determined to be 63 m$^2$/g and the pore volume 0.295 cc/g. The powder XRD pattern is set out below:

| XRD Lines for Ni$_2$AlBO$_5$ | | |
|---|---|---|
| Interplanar Spacing[1] d, Å | Assigned Strength[2] | Relative Intensity |
| 5.01 ± 0.2 | M | 42 |
| 4.55 ± 0.10 | M | 50 |
| 3.66 ± 0.08 | W | 21 |
| 2.72 ± 0.05 | W | 17 |
| 2.64 ± 0.05 | W | 15 |
| 2.51 ± 0.04 | S | 95 |
| 2.47 ± 0.04 | VS | 100 |
| 2.29 ± 0.03 | M | 28 |
| 2.28 ± 0.03 | W | 19 |
| 2.27 ± 0.03 | W | 14 |
| 2.12 ± 0.03 | W | 22 |
| 2.10 ± 0.03 | W | 17 |
| 2.08 ± 0.03 | W | 23 |
| 1.99 ± 0.03 | M | 32 |
| 1.87 ± 0.03 | M | 40 |
| 1.72 ± 0.03 | VW | 10 |
| 1.54 ± 0.02 | W | 22 |
| 1.47 ± 0.02 | W | 22 |
| 1.46 ± 0.02 | M | 31 |
| 1.44 ± 0.02 | W | 19 |

[1]Angstroms
[2]VW = very weak; W = weak; M = medium; S = strong; VS = very strong

EXAMPLE 7

The preparation of Example 6 was repeated with the dry solid being calcined to a temperature of 1020° C. for 8 hours. This product was analyzed by powder XRD, ICP elemental analysis and BET surface analysis. Elemental analysis showed 48% nickel, 10.5% aluminum, and 4.4% boron. The BET surface area was determined to be 5 m$^2$/g.

COMPARATIVE EXAMPLE A

The ingredients placed into a Waring blender were 16.6 g Ni(NO$_3$)$_2$—6H$_2$O (0.0571 mol) dissolved in 20 mL warm distilled water, 567.7 g of alumina sol (7.6% alumina, 0.428 mol) and 10.6 g H$_3$BO$_3$ (0.172 mol) dissolved in 50 mL warm distilled water. The contents of the blender were mixed for 2 minutes. After mixing the mixture had a pH of 5.0. Ammonium hydroxide, 5.6 mL, was added with mixing to the blender and the mixture was blended for 4 minutes. The mint green gel had a final pH of 5.5. The gel was placed evenly on a 35 cm×45 cm plastic tray and allowed to air dry. A portion, 87.92 g, of the material was placed in a vacuum oven at 120° C., 0.3 atm pressure with a nitrogen purge and dried to a final weight of 76.51 g. A portion of this solid, 58.98 g, was calcined according to the following program:

$$120\ C.\ \xrightarrow{1\ hr}\ 165\ C.\ \xrightarrow{3\ hrs}\ 780\ C.\ \xrightarrow{8\ hrs}$$

$$780\ C.\ \xrightarrow{3\ hrs}\ 165\ C.\ \xrightarrow{1\ hr}\ 120\ C.\ \xrightarrow{1\ hr}\ 25\ C.$$

This resulted in 38.0 g of calcined material.

COMPARATIVE EXAMPLE B

The ingredients placed into a Waring blender were 29.1 g Ni(NO$_3$)$_2$ dissolved in 30 mL warm distilled water and 134.2 g of alumina sol (7.6% alumina, 0.100 mol) with 100 mL distilled water. The contents of the blender were mixed 6 minutes. After blending the mixture had a pH of 5.0. The mint green gel was placed evenly on a 35 cm×45 cm plastic tray and allowed to air dry. A portion, 24.18 g, of the material was placed in a vacuum oven at 120° C., 0.3 atm pressure with a nitrogen purge and dried to a final weight of 19.26 g. A portion of this solid, 5.50 g, was calcined according to the following program:

$$120\ C.\ \xrightarrow{1\ hr}\ 350\ C.\ \xrightarrow{4\ hrs}\ 1020\ C.\ \xrightarrow{12\ hrs}$$

$$1020\ C.\ \xrightarrow{4\ hrs}\ 350\ C.\ \xrightarrow{1\ hr}\ 25\ C.$$

This resulted in 2.88 g of calcined material. The material was identified by its XRD pattern which matched that of nickel aluminate.

COMPARATIVE EXAMPLE C

The ingredients placed into a mortar were 29.1 g Ni(NO$_3$)$_2$—6H$_2$O (0.100 mol) and 4.1 g H$_3$BO$_3$ (0.067 mol) and ground together with a pestle as quickly as possible because the mixture is hygroscopic. A portion, 7.17 g, of the ground material was placed in a calcination oven and calcined according to the following program:

$$120\ C.\ \xrightarrow{1\ hr}\ 350\ C.\ \xrightarrow{4\ hrs}\ 1020\ C.\ \xrightarrow{12\ hrs}$$

$$1020\ C.\ \xrightarrow{4\ hrs}\ 350\ C.\ \xrightarrow{1\ hr}\ 25\ C.$$

The 2.00 g of calcined material was identified by its XRD pattern which matched that of nickel borate.

EXAMPLES 8-12 AND COMPARATIVE EXAMPLES D-F

In these examples the catalysts prepared in Examples 1, 2, 3, 5 and 6 and Comparative Examples A, B and C were tested as catalysts for conversion of methylbenzoate (PhCOOMe), to benzaldehyde (PhCHO), in Examples 8, 9, 10, 11 and 12 and Comparative Examples D, E and F respectively.

For screening, the catalyst was ground and sieved to 18/35 mesh and 5.00 g was placed on a quartz frit in a 19 mm OD quartz reactor tube. A 5 mm OD quartz thermowell was fitted axially in the catalyst bed. The reactor tube was placed in an electrically heated tube furnace with the catalyst bed centered in the heated zone and heated to the desired reaction temperature under nitrogen flow. The gas supply was then switched to hydrogen and the flow of liquid reactant was begun. The hydrogen flow rate was set to 30 mL/min using a Brooks mass flow controller. The methylbenzoate was introduced through a stainless steel tube which ended against the thermowell, allowing the liquid to flow down the thermowell and vaporize above the catalyst bed. Generally, the liquid flow rate was set to 0.0148 mL/min with a syringe pump. Assuming a catalyst density of 1 g/mL, this gives a space velocity WHSV=0.18 and a contact time of 5 sec at 350° C. The conversion and selectivity reported for hydrogenation of methylbenzoate over catalysts containing nickel for Examples 9-11 were obtained at WHSV of 0.05 to 0.06 hr$^{-1}$. At calculated WHSV of 0.119 hr$^{-1}$ a conversion of 30% and a selectivity of 60% were obtained in Example 9. At calculated WHSV of 0.117 hr$^{-1}$ a conversion of 6.5% and a selectivity of 21% were obtained in Example 10. At calculated WHSV of 0.115 hr$^{-1}$ a conversion of 25.5% and a selectivity of 24% were obtained in Example 11.

Products from runs of about 2 hrs duration were collected in a dry ice cooled trap at the outlet of the reactor. The liquid collected was analyzed by GC using a Superox capillary column. The conversion and selectivity data given below was based on uncorrected FID area percents of methylbenzoate and benzaldehyde. Methanol was also detected in all cases, but it was not used in quantization because of the detector's relative insensitivity to it. Other by-products were benzene, toluene, small amounts of several unidentified heavies, and occasionally benzyl alcohol. Only benzene and toluene were present in large amounts.

| Example | Catalyst | Temp | PhCOOMe conversion | PhCHO selectivity |
|---|---|---|---|---|
| 8 | NiAlBO$_4$ Example 1 | 350° C. | 6.4% | 73% |
|  |  | 375 | 12.3 | 70 |
|  |  | 400 | 24.8 | 70 |
| 9 | NiAlBO$_4$ Example 2 | 350 | 69.0 | 78 |
| 10 | NiAlBO$_4$ Example 3 Nitric acid Leached | 350 | 20.0 | 58 |
| 11 | NiAlBO$_4$ Example 5 Th | 350 | 32.0 | 22 |
| 12 | Ni$_2$AlBO$_5$ Example 6 | 350 | 4.8 | 49 |
|  |  | 375 | 9.4 | 54 |
|  |  | 400 | 21.6 | 40 |
| D | Amorphous Example A | 350 | 2.5 | 24 |
|  |  | 375 | 7.3 | 26 |
|  |  | 400 | 24.1 | 19 |
| E | NiAl$_2$O$_4$ Example B | 350 | 26.8 | 16 |
|  |  | 400 | 78.2 | 36 |
| F | Ni$_3$(BO$_2$)$_2$ Example C | 350 | 2.4 | 0 |
|  |  | 400 | 5.2 | 3 |

Hydrogenation of Methyl Benzoate over Catalysts Containing Nickel

After use in Example 12 the catalyst prepared as in Example 6 was again analyzed. Comparative data for surface analysis, given below, indicate no substantial change in the character of the catalyst during use.

Surface Analysis of Catalyst Before and After Use in Hydrogenation of Methyl Benzoate
Analysis in Atom Percent

| Element | Before Use | After Use |
|---|---|---|
| Carbon | 20.3 | 16.1 |
| Oxygen | 42.7 | 44.4 |
| Aluminum | 13.5 | 14.8 |
| Boron | 10.6 | 12.6 |
| Nickel | 11.7 | 11.9 |

EXAMPLE 13

In this example, inorganic solid material prepared as in Example 6 was tested as a catalyst for dehydrogenation of ethylbenzene to styrene.

The solid material described above was ground and sieved to 12-24 mesh. A 24.7 g, 41.0 cc sample was placed into a low-nickel, stainless steel tubular reactor which was operated isothermally at 1100° F. Ethylbenzene and steam were fed though the reactor simultaneously. Downstream from the reactor a condenser and gas-liquid-separator collected product samples during a 24-hour period. The results are summarized as below:

Temperature 587° C. (1100° F.)
LHSV = 1.0/hr
Steam to hydrocarbon (wt. to wt.) = 2.0
Conversion 22.4%
Selectivity 73%
Benzene/toluene ratio = 2:1
Yield = 16%

EXAMPLE 14

A crystalline inorganic material was prepared containing cobalt, aluminum, boron and oxygen in accordance with this invention by a process including five steps: 1) combining ingredients in a liquid medium, 2) gelling the combined ingredients, 3) removing substantially all the liquid to obtain a dry solid, 4) calcining the dry solid, and 5) washing the calcined solid.

The ingredients placed into a Waring blender were 203.7 g Co(NO$_3$)$_2$—1H$_2$O (0.700 mol) dissolved in 200 mL 198.7 g of PHF alumina sol (7.7% AL$_2$O$_3$ by wt., 0.150 mol) and 18.5 g H$_3$BO$_3$ (0.300 mol) dissolved in 90 mL of warm distilled water. The contents of the blender were mixed one minute on low and on minute on high speed. The resulting deep raspberry colored thick gel had a pH of 3.5. Addition of 5.2 mL of NH$_4$OH and subsequent blending for one minute resulted in a thinner grape-raspberry colored gel which had a pH of 4.5-5.0. Continued blending for six minutes, and air drying on a 35 cm × 45 cm tray resulted in 192.9 g of material. Drying this material in a vacuum oven for 21 hrs at 0.3 atm and 120° C. resulted in 81.4 g of large dark purple chunks. Part of this purple solid, 9.35 g, was calcined in air using the following program:

$$120\ C. \xrightarrow{2\ hr} 350\ C. \xrightarrow{3\ hrs} 850\ C. \xrightarrow{8\ hrs}$$

$$850\ C. \xrightarrow{3\ hrs} 350\ C. \xrightarrow{1\ hr} 25\ C.$$

This product was analyzed by powder XRD, ICP elemental analysis and BET surface analysis. Elemental analysis showed 50.0% cobalt, 9.5% aluminum, and 4.6% boron which indicates that the crystalline material has the chemical composition Co$_2$AlBO$_5$. The BET surface area was determined to be 6 m$^2$/g, with a pore volume of 0.018 cc/g. The powder XRD pattern is set out below:

XRD Lines for Co$_2$AlBO$_5$

| Interplanar Spacing[1] d, Å | Assigned Strength[2] | Relative Intensity |
|---|---|---|
| 5.03 ± 0.2 | M | 54 |
| 4.60 ± 0.1 | M | 36 |
| 3.68 ± 0.08 | W | 18 |
| 2.78 ± 0.05 | VW | 10 |
| 2.68 ± 0.05 | VW | 10 |
| 2.52 ± 0.04 | VS | 100 |
| 2.32 ± 0.04 | W | 23 |
| 2.30 ± 0.04 | W | 15 |
| 2.13 ± 0.04 | W | 18 |
| 2.12 ± 0.04 | W | 13 |
| 2.11 ± 0.04 | W | 18 |
| 2.02 ± 0.03 | W | 20 |
| 1.89 ± 0.03 | M | 28 |
| 1.83 ± 0.02 | VW | 8 |
| 1.75 ± 0.02 | VW | 8 |
| 1.69 ± 0.02 | VW | 5 |
| 1.56 ± 0.02 | W | 18 |
| 1.50 ± 0.02 | W | 15 |
| 1.47 ± 0.02 | W | 15 |

-continued

| XRD Lines for $Co_2AlBO_5$ | | |
|---|---|---|
| Interplanar Spacing[1] d, Å | Assigned Strength[2] | Relative Intensity |
| 1.46 ± 0.02 | W | 13 |
| 1.43 ± 0.02 | VW | 8 |
| 1.37 ± 0.02 | W | 13 |

[1]Angstroms
[2]VW = very weak; W = weak; M = medium; S = strong; VS = very strong Material prepared as in this Example was tested as a catalyst for the hydrogenation of methylbenzoate to benzaldehyde as described above. The material gave a conversion of 6% and a selectivity to benzaldehyde of 51%.

The oxidation capability of material prepared as in this Example was tested by running atmospheric oxidations of p-xylene with air at a temperature of 120° C. in a glass reactor equipped with a glass frit for supporting the solid catalyst and dispersing the air. Solid catalyst, 1.12 g, and p-xylene, 80 mL, were placed in the glass reactor. Air flow was controlled at 100 mL/min during a 6-hour reaction period. Oxidation activity was observed with an oxygen monitor, calibrated with air to read 20.9%. The monitor reading doped to 20.5% oxygen during the oxidation. The liquid product was a very pale yellow and contained only 0.05 ppm dissolved cobalt.

EXAMPLES 15-17

These examples describe the preparation of solid solutions containing nickel, cobalt, aluminum, boron, and oxygen prepared according to this invention.

Solutions of nickel nitrate hexahydrate (105.9 g dissolved in 110 mL of warm deionized water), cobalt nitrate hexahydrate (10.59 dissolved in 20 mL warm deionized water) and boric acid (61.8 g in 300 mL warm deionized water) were added to 110.0 g of $Al_2O_3$ PHF alumina sol in a Waring blender. The mixture was blended for 3 minutes, yielding a mixture with a pH of 3.5. Addition of 45 mL of ammonium hydroxide, with subsequent blending at low speed, yielded a material with a pH of 6.4. The thin, gel-like material was poured out onto a plastic tray and allowed to air dry. The air dried sample, 151.5 g, was vacuum dried at 120° C. and 0.3 atm for 15 hrs with a nitrogen purge. The resulting product had a weight of 124.3 g. This sample was calcined and labeled Example 15.

Solutions of nickel nitrate hexahydrate (87.2 g, 0.30 mol, in 90 mL warm deionized water), cobalt nitrate hexahydrate (29.1 g, 0.10 mol, in 30 mL warm deionized water), and boric acid (61.8 g, 1.00 mol, in 300 mL warm deionized water) were added to a Waring blender with 119.2 g of an 8.56% $Al_2O_3$ PHF alumina sol (0.10 mol $Al_2O_3$). The material was blended for 3 minutes on low speed, stirred, and blended on low speed for an additional 30 seconds. The mixture has a pH of approximately 4. Addition of 47 mL of ammonium hydroxide raised the pH to about 6.4. The thin gel-like material was poured out onto a 35 cm×45 cm plastic tray and allowed to air dry. The air dried material, 165.5 g, was vacuum dried at 120° C. and 0.3 atm. for 60 hrs with a nitrogen purge. The yield was 124.9 g.

A 26.52 g portion was calcined in air for two weeks at 830 C, yielding 14.54 g. of calcined solids. The sample was removed from the oven and ground with a mortar and pestle. A portion of the ground solids, 11.69 g, was recalcined at 830 C for an additional 15 days. The final weight was 11.3 g. This sample was calcined and labeled Example 16.

Solutions of nickel nitrate hexahydrate (58.2 g, 0.20 mol, dissolved in 60 mL of warm deionized water), cobalt nitrate hexahydrate (58.2 g, 0.20 mol, dissolved in 60 mL of warm deionized water), and boric acid (61.8 g, 1.00 mol, in 300 mL of warm deionized water) were added in 119.2 g of an 8.56% $Al_2O_3$ PHF alumina sol (0.10 mol $Al_2O_3$) into a Waring blender. The mixture was blended for 3 minutes. Addition of 46 mL of ammonium hydroxide, with subsequent blending at low speed, yielded a mixture with a pH of 6.2. The thin, gel-like material was poured out onto a 35 cm×45 cm plastic tray and allowed to air dry. The air dried sample, 166.6 g, was vacuum dried at 120° C. and 0.3 atm with a nitrogen purge for 60 hrs. The resultant product had a weight of 115.6 g. A 27.55 g sample was calcined as above, yielding 15.9 g of product. A 7.74 g sample, recalcined as above after grinding, yielded 7.45 g. This sample was calcined and labeled Example 17.

The principal lines of the XRD patterns for the five samples prepared as in Examples 6, 15-17, and 14 are set out below:

| Principal XRD Lines for Solid Solutions | | | | |
|---|---|---|---|---|
| Example no. | | | | |
| 6 | 15 | 16 | 17 | 14 |
| Ni/Co | | | | |
| 1.0/0.0 | 0.9/0.1 | 0.75/0.25 | 0.5/0.5 | 0.0/1.0 |
| d/RI[1] | | | | |
| 5.01/42 | 5.01/42 | 5.02/46 | 4.98/41 | 5.03/54 |
| 4.55/50 | 4.56/52 | 4.56/51 | 4.54/41 | 4.60/36 |
| 3.66/21 | 3.66/18 | 3.67/22 | 3.65/22 | 3.68/18 |
| 2.51/95 | 2.51/76 | 2.51/91 | 2.50/100 | 2.52/49 |
| 2.47/100 | 2.47/100 | 2.48/100 | 2.48/80 | 2.51/100 |
| 2.29/28 | 2.29/26 | 2.30/28 | 2.30/28 | 2.32/23 |
| 1.99/32 | 1.99/26 | 2.00/27 | 2.00/29 | 2.02/20 |
| 1.87/40 | 1.87/24 | 1.87/31 | 1.87/34 | 1.89/28 |

[1]Interplanar Spacing, Angstroms/Relative Intensity

Five samples prepared as in Examples 6, 15-17, and 14 were analyzed for unit cell parameters, a, b, and c, and cell volumes, V, calculated as the product a.b.c. The cell volumes change smoothly with mole fraction of the metal oxide phase. The data appear below:

| Orthorhombic Cell Dimensions in $(Co:Ni)_2Al(BO_3)O_2$ Phases | | | | |
|---|---|---|---|---|
| Preparation | a, Å | b, Å | c, Å | V, Å$^3$ |
| Ni | 9.0934 (29) | 12.0035 (32) | 2.9411 (7) | 321.0 |
| $Ni_{0.9}:Co_{0.1}$ | 9.0828 (20) | 12.0124 (44) | 2.9451 (7) | 322.1 |
| $Ni_{0.75}:Co_{0.25}$ | 9.1443 (15) | 12.0090 (39) | 2.9509 (8) | 324.1 |
| $Ni_{0.5}:Co_{0.5}$ | 9.1685 (49) | 11.9996 (125) | 2.9586 (26) | 325.4 |
| Co | 9.2041 (6) | 12.0376 (8) | 2.9997 (3) | 332.4 |

[1]Angstroms

EXAMPLE 18

The ingredients placed into a Waring blender were 0.36 g zinc nitrate hydrate (0.00125 mol), 72.3 g Ni(NO$_3$)$_2$—6H$_2$O (0.249 mol) dissolved in 70 mL warm deionized water, 178.7 g of alumina sol (8.6% alumina, 0.150 mol) and 74.2 g H$_3$BO$_3$ (1.2 mol) dissolved in 370 mL warm deionized water. The contents of the blender were mixed for 2 minutes. After mixing the mixture had a pH of 3.5. Ammonium hydroxide, 75 mL, was added with mixing to the blender and the mixture was blended for 3 minutes. The thin gel had a final pH of 8.5. The gel was placed evenly on a 35 cm×45 cm plastic tray and allowed to air dry. The dry solid, 141.4 g, was placed in a vacuum oven at 120° C., 0.3 atm pressure with a nitrogen purge and dried for 20 hours. After drying a portion of the dry solid, 45.8 g, was calcined according to the following program:

$$120\ C. \xrightarrow{2\ hr} 250\ C. \xrightarrow{3\ hrs} 780\ C. \xrightarrow{8\ hrs}$$

$$780\ C. \xrightarrow{2\ hrs} 250\ C. \longrightarrow 25\ C.$$

This resulted in 27.7 g of calcined material which had a smoky blue color. The large chunks of calcined material were powdered and placed in a 1-liter round bottom flask with 500 mL of deionized water and refluxed for 3 hours. The undissolved solid was recovered by vacuum filtration and dried for 18 hours in a vacuum oven with a nitrogen purge at a temperature of 120° C. and a pressure of 0.3 atm. This solid material was tested as a catalyst for hydrogenation of methylbenzoate as described hereinabove. At a WHSV of 0.062 hr$^{-1}$ and a reaction temperature of 350° C., the conversion of methylbenzoate was 41.5% and selectivity to benzaldehyde was 86%.

EXAMPLE 19

This example describes the preparation of a solid solution containing nickel, cobalt, aluminum, boron, and oxygen prepared according to this invention.

Solutions of nickel nitrate hexahydrate (185.2 g, 0.636 mol, dissolved in 180 mL of warm deionized water), cobalt nitrate hexahydrate (18.5 g, 0.0636 mol, dissolved in 20 mL of warm deionized water) and boric acid (49.5 g, 0.8 mol, in 250 mL warm deionized water) were added to 172.3 g of Al$_2$O$_3$ PHF alumina sol in a Waring blender. The mixture was blended for 3 minutes at low speed, yielding a mixture with a pH of 4. Addition of 35 mL of ammonium hydroxide, with subsequent blending at low speed at low speed, yielded a material with a pH of 6.4. This raspberry colored gel was poured out onto a plastic tray and allowed to air dry. The air dried sample, 167.5 g, was vacuum dried at 120° C. and 0.3 atm for 18 hrs with a nitrogen purge. The resulting product had a weight of 167.5 g. A portion of this solid, 19.21 g, was calcined according to the following program:

$$120\ C. \xrightarrow{2\ hr} 300\ C. \xrightarrow{3\ hrs} 900\ C. \xrightarrow{8\ hrs}$$

$$900\ C. \xrightarrow{3\ hrs} 300\ C. \longrightarrow 25\ C.$$

This resulted in 10.1 g of calcined material. This product was analyzed by powder XRD, ICP elemental analysis and BET surface analysis. The XRD pattern was essentially the same as the pattern of Table IV. Elemental analysis showed 40.0% cobalt, 4.5% nickel, 10.6% aluminum, and 9.8% boron. The BET surface area was determined to be 2.2 m$^2$/g.

What is claimed is:

1. A crystalline material comprising aluminum, boron, oxygen and nickel having an X-ray diffraction powder pattern comprising significant lines substantially as follows

| Interplanar Spacing d, Å | Assigned Strength |
|---|---|
| 6.41 ± 0.2 | weak, |
| 4.09 ± 0.10 | medium, |
| 2.90 ± 0.08 | medium, |
| 2.53 ± 0.05 | medium, |
| 2.50 ± 0.05 | very strong, |
| 1.92 ± 0.05 | weak, |
| 1.74 ± 0.04 | weak, |
| 1.55 ± 0.04 | weak, |
| 1.50 ± 0.04 | weak, and |
| 1.46 ± 0.03 | weak. |

2. The crystalline material of claim 1 with a binder.

3. The crystalline material of claim 1 with from about 0.05 to about 50 wt % of at least one metallo element selected from the group consisting of Groups IA, IIA, IIB, and IIIB of the Periodic Table based on the weight of crystalline material.

4. The composition of claim 1 comprising crystalline NiAlBO$_4$.

5. The process of making the crystalline material of claim 1 which comprises dispersing in a liquid medium a source of alumina, a source of boria, and a source of nickel (II) ions, removing substantially all the liquid to form a superficially dry solid, and calcining the superficially dry solid at a temperature in a range from about 700° C. to about 1100° C.

6. The process of claim 5, wherein the molar ratio of the source of Ni(II) ions to the source of boria, in terms of oxides calculated as NiO/B$_2$O$_3$, is about 0.1 to about 100, and the molar ratio of the source of alumina to the source of boria, in terms of oxides calculated as Al$_2$O$_3$/B$_2$O$_3$, is about 0.01 to about 10.

7. The process of claim 6, wherein the NiO/B$_2$O$_3$ molar ratio is about 0.15 to about 40, the Al$_2$O$_3$/B$_2$O$_3$ mole ratio is about 0.02 to about 5, and the pH range is about 3 to about 10.

8. The process of making the crystalline material of claim 4, which comprises forming an aqueous composition comprising a source of nickel(II) ions, a source of alumina, and a source of boria, at a pH in a range from about 4 to about 9, drying the mixture to form a superficially dry solid, and calcining the dry solid at a temperature in a range from about 700° C. to about 1100° C. to form a calcined solid.

9. The process of claim 8 wherein the aqueous composition further comprises aqueous ammonia.

* * * * *